(12) United States Patent
Cigaina et al.

(10) Patent No.: US 10,441,799 B2
(45) Date of Patent: Oct. 15, 2019

(54) SET COMPRISING A TOTALLY IMPLANTABLE DEVICE FOR ELECTRONEUROMODULATION AND AN IMPLANTATION TOOL OF SAID DEVICE

(71) Applicant: Valerio Cigaina, Cortina D'ampezzo (Belluno) (IT)

(72) Inventors: Valerio Cigaina, Cortina D'ampezzo (IT); Paolo Fabris, Thiene (IT); Simone Cigaina, Villorba (IT)

(73) Assignee: Valerio Cigaina, Cortina d'ampezzo (Belluno) (IT)

( * ) Notice: Subject to any disclaimer, the term of this patent is extended or adjusted under 35 U.S.C. 154(b) by 498 days.

(21) Appl. No.: 15/038,767

(22) PCT Filed: Nov. 28, 2014

(86) PCT No.: PCT/EP2014/075895
§ 371 (c)(1),
(2) Date: May 24, 2016

(87) PCT Pub. No.: WO2015/079005
PCT Pub. Date: Jun. 4, 2015

(65) Prior Publication Data
US 2016/0375256 A1 Dec. 29, 2016

(30) Foreign Application Priority Data
Nov. 28, 2013 (IT) .............................. MI2013A1992

(51) Int. Cl.
| *A61B 17/34* | (2006.01) |
| *A61N 1/372* | (2006.01) |
| *A61N 1/375* | (2006.01) |
| *A61N 1/05* | (2006.01) |

(Continued)

(52) U.S. Cl.
CPC ...... *A61N 1/37205* (2013.01); *A61B 17/3468* (2013.01); *A61N 1/0551* (2013.01);
(Continued)

(58) Field of Classification Search
CPC .... A61N 1/36–1/3993; A61N 1/0507–1/0514; A61N 1/36007;
(Continued)

(56) References Cited

U.S. PATENT DOCUMENTS

| 6,165,180 A | 12/2000 | Cigaina et al. |
| 6,591,838 B2 * | 7/2003 | Durgin ............. A61B 17/00234 128/898 |

(Continued)

FOREIGN PATENT DOCUMENTS

| FR | 2756493 | 6/1998 |
| WO | 20020089655 | 11/2002 |
| WO | 20120150348 | 11/2012 |

OTHER PUBLICATIONS

International Search Report dated Feb. 6, 2015; International Application No. PCT/EP2014/075895; International Filing Date: Nov. 28, 2014; 5 pages.

(Continued)

*Primary Examiner* — Jonathan A Hollm
(74) *Attorney, Agent, or Firm* — Blank Rome LLP

(57) ABSTRACT

The set comprises a totally implantable device (1) for electroneuromodulation for the electric stimulation of the nervous tissue of the wall of the stomach and/or another neuroreceptive biological tissue and an implantation tool (2) of the device (1), the tool (2) comprising an axially hollow longitudinal containment body (6) for said device (1) and a needle (12) incorporated into said containment body (6) and having a tip (13) that projects forwards to a sharp front end (7) of the containment body (6), said needle (12) being connected to a supply conduit (15) of a fluid injectable from said needle (12) into the tissue for the creation of a localized tissue swelling (4) in which said device (1) can be positioned.

7 Claims, 7 Drawing Sheets

(51) Int. Cl.
- *A61N 1/36* (2006.01)
- *A61N 1/378* (2006.01)
- *A61B 17/00* (2006.01)

(52) U.S. Cl.
CPC ....... *A61N 1/3605* (2013.01); *A61N 1/36007* (2013.01); *A61N 1/375* (2013.01); *A61N 1/3756* (2013.01); *A61N 1/3787* (2013.01); *A61B 2017/0034* (2013.01); *A61B 2017/00269* (2013.01); *A61B 2017/00402* (2013.01); *A61B 2017/00818* (2013.01)

(58) Field of Classification Search
CPC .......... A61N 1/36128–1/36196; A61F 5/0003; A61F 5/0013; A61F 5/0026; A61F 5/0069; A61F 5/0089; A61F 2005/0016–2005/0023; A61B 5/042–5/04288; A61B 2018/1475

See application file for complete search history.

(56) References Cited

U.S. PATENT DOCUMENTS

| | | | |
|---|---|---|---|
| 7,096,070 B1 | 8/2006 | Jenkins et al. | |
| 7,361,135 B2 * | 4/2008 | Drobnik | A61M 37/0069 600/3 |
| 2004/0093039 A1 * | 5/2004 | Schumert | A61B 5/4255 607/40 |
| 2006/0089633 A1 | 4/2006 | Bleich et al. | |

OTHER PUBLICATIONS

Written Opinion dated Feb. 6, 2015; International Application No. PCT/EP2014/075895; International Filing Date: Nov. 28, 2014; 6 pages.

English translation; French Application No. FR2756493; Publication Date: May 2, 2013; 8 pages.

\* cited by examiner

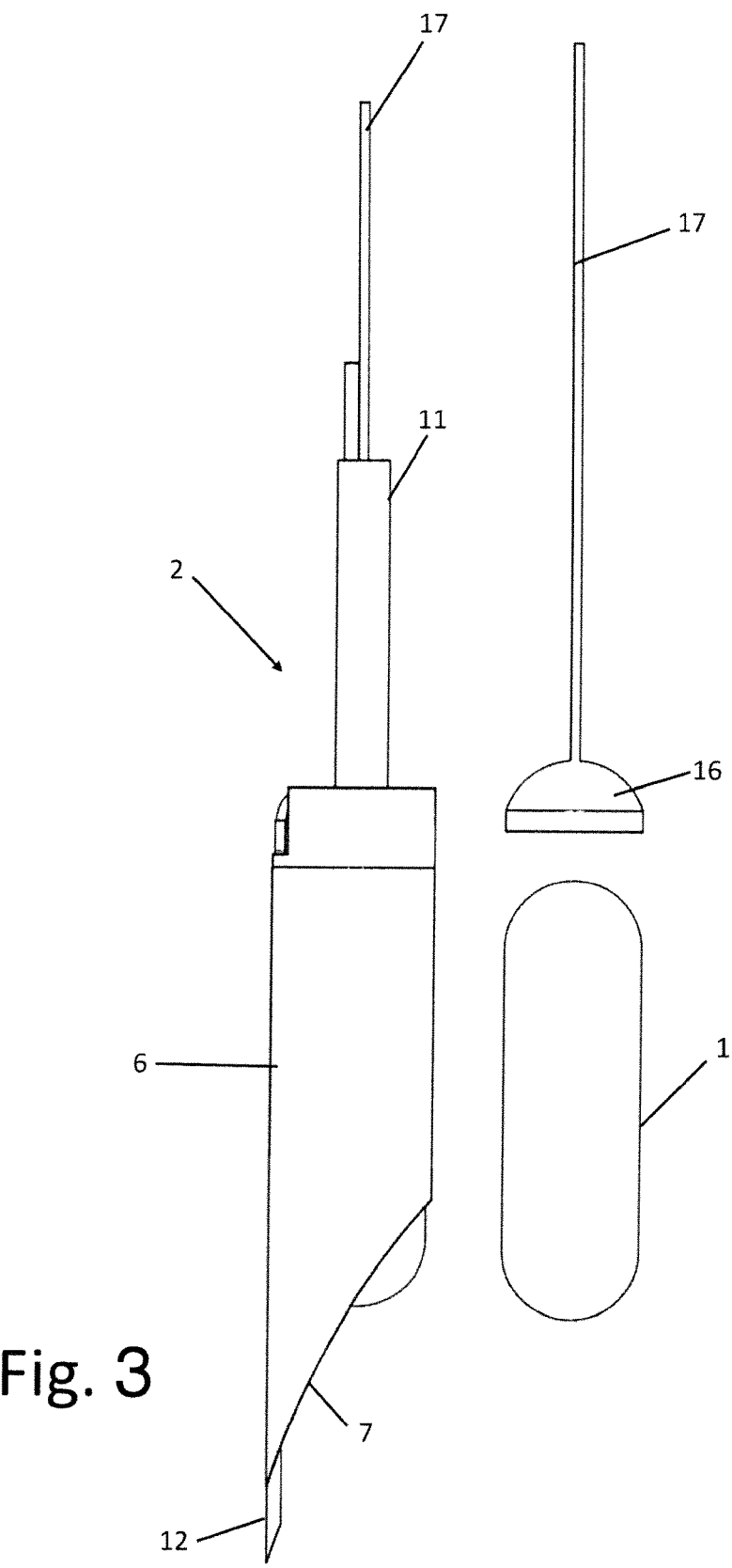

Fig. 7
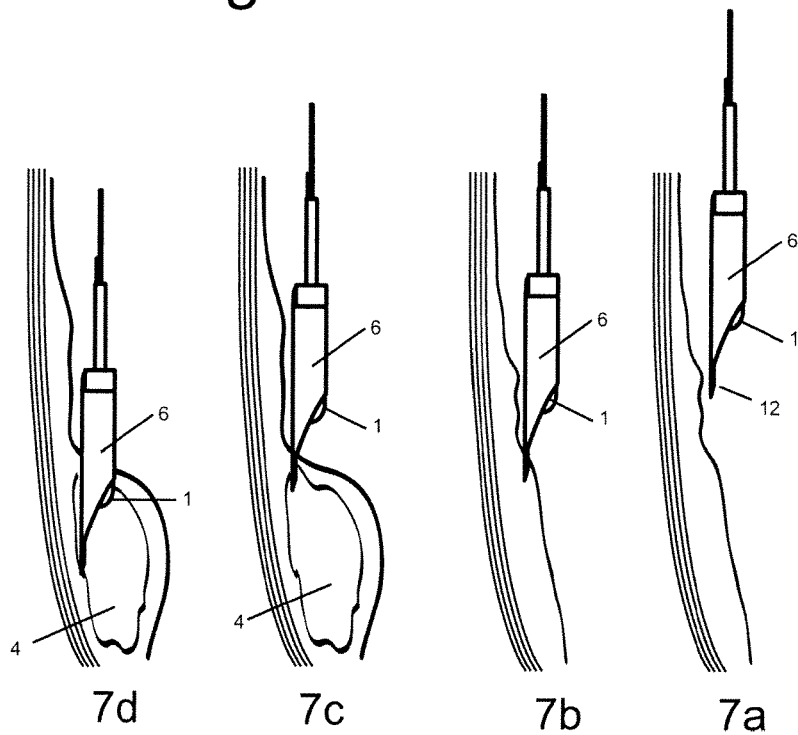
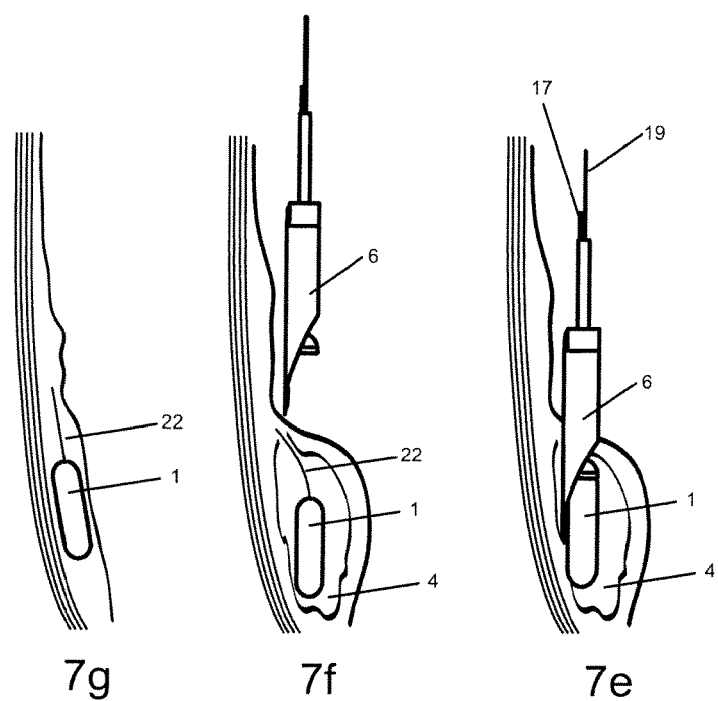

SET COMPRISING A TOTALLY IMPLANTABLE DEVICE FOR ELECTRONEUROMODULATION AND AN IMPLANTATION TOOL OF SAID DEVICE

RELATED APPLICATIONS

This application is a U.S. national phase application of International Application No. PCT/EP2014/075895, filed Nov. 28, 2014; which application claims priority to Italy Application No. MI2013A 001992, filed Nov. 28, 2013. Each of the above-identified related applications are incorporated by reference.

The present invention relates to a set comprising a totally implantable device for electroneuromodulation and an implantation tool of said device.

In particular it relates to a totally implantable device able to electrically stimulate the nervous tissue of the wall of the stomach and/or other neuroreceptive tissues of the human body, equipped with an independent power supply system integrated into the device itself, and an implantation tool of such a device.

BACKGROUND OF THE INVENTION

The field of the electric stimulation of tissues has been recently extended to include devices that electrically stimulate many organs, intra- and extra-abdominal, through electrodes implanted in the tissue.

The electrical connection between the pulse generator and the electrodes implanted in the organ or tissue of the body can be obtained through one or more wires defined as electrocatheters (leads).

Recently some studies have highlighted that electric stimulation of the stomach effectively combats obesity, GE arterial hypertension, type 2 diabetes, depressive disorder and even psoriasis, all diseases marked by orthosympathetic hypertone.

Scientific research is committed to the effort for understanding the operating mechanisms, and the areas, of electric stimulation in the modulation of the Autonomic Nervous System in pathological processes associated with an imbalance thereof.

A prestigious publication (Gene-Jack) describes the detectable modifications in some areas of the brain, mapped using brain imaging, in patients subjected to electric stimulation of the stomach.

This discovery reinforces the concept that the stomach, like other organs or body sites, need not be considered as the receiver of the stimulation, but as a means through which information can be sent to the Central Nervous System (through electrical code pulses applied to the nervous fibres contained in the gastric wall or in other sites), the real final receiver. Just as for the stomach, it is desirable to also have other centres of stimulation that can be used for this purpose, present in other areas of the human body.

The stimulation of these areas is exploited to correct pathological decompensations of the sympathetic/parasympathetic system.

The adjustment of all the electric stimulation devices which act in order to correct these decompensations is based on heart rate variability.

This heart rate variability (HRV) data can also be used for the early diagnosis of possible cardiovascular and/or metabolic events.

All electric stimulators or pacemakers currently in use, both for gastric stimulation and for stimulation of the intra-abdominal organs and other neurological tissues, need one or more connecting electrocatheters, with different shapes and sizes, between the appliance and the organ or the target tissue of the stimulation, a battery as a source of electrical energy for the stimulation, and a surgical operation for the implantation process.

The shape of the stimulator forces the surgeon to have to make a visible cut on the skin of the abdomen or another site of the body, which is necessary in order to create the subcutaneous pocket in which the stimulator will be housed.

Clinical experience has highlighted that the presence of the subcutaneous pocket and that of the electrocatheter can cause technical problems during the course of the therapy.

In particular, the electrocatheter entails various drawbacks due to the possibility of breaking, its displacement, penetration, erosion and/or perforation of the organ at the housing point, the increase in the anaesthesiological and surgical times attributed to the operations required for anchoring it to the tissue, its risk of bending or stinging near the pacemaker or getting tangled with surrounding organs.

The pulse generator located inside a subcutaneous pocket, on its part, can influence or prevent the normal movement of the patient, be rejected, suffer traumas with lesions of the overlying skin and therefore have to be removed early, be unsightly since it is visible at the advanced weight loss stage or make the abdominal housing scar visible, increase the general anaesthetic time and that of the implantation surgery and increase surgical times. Once the battery is drained, it must also be replaced, hence requiring another surgical operation.

SUMMARY OF THE INVENTION

The technical task of the present invention is, therefore, to provide a set comprising a totally implantable device for electroneuromodulation and an implantation tool of said device which obviate the above-described technical drawbacks of totally implantable stimulators of the prior art.

Within the scope of this technical task an object of the invention is to provide a system for the electric stimulation of a body and/or neurological site that eliminates the drawbacks connected both with the presence of the subcutaneous pocket for its placement and the presence of one or more electrocatheters.

Within the scope of this technical task an object of the invention is to provide a system for the electric stimulation of a body and/or neurological site that eliminates the drawbacks connected with the presence of a stimulator that needs to be periodically recharged or replaced due to having a drained battery, up to now the only source of the energy necessary for stimulation.

Another object of the invention is to provide a system for the electric stimulation of a body and/or neurological site equipped with an internal micro generator even coupled with charge storage devices (batteries, capacitors, etc.) and/or various electronic circuits, microchips and micro storage and/or data transmission devices.

Another object of the invention is to provide a system for the electric stimulation of a body and/or neurological site that eliminates the drawbacks connected both with the need for a surgical operation for its installation and with the complications and skin marks resulting therefrom.

Another aim of the invention is to provide a device that can independently stimulate the affected tissues and be helped in its operation by external devices that can be used independently by the patient, able to amplify and/or make the stimulation even more effective.

Such devices may be of a magnetic nature with mechanical movement, ultrasound generators able to excite piezoelectric systems or electrical generators of magnetic fields with variable intensities and times.

In all cases this system can be assisted by IT supports, even integrated into the components, adapted to determine a precise and more effective stimulation, based on the calculation of variables introduced by an external operator or independently collected by the appliance.

Another object of the invention is to provide a system able to collect information regarding the patient's heart rate and send it to an external device with the aim of determining better stimulation parameters and to allow the attending physician to have data for producing the diagnoses also or exclusively based on the patient's heart rate and variability.

Another object of the invention is to provide a system able to collect information regarding the patient's body functions and send it to an external device, with the aim of determining the stimulation parameters better and/or allowing the attending physician to have data for producing the diagnoses based on or that can be helped by the collected data.

Another object of the invention is to provide a system able to facilitate the insertion and positioning operations of a device for the electric stimulation of tissues through an implantation tool operating through a specific procedure without needing a surgical operation and the relative consequences e.g. general anaesthetic.

The technical task, as well as these and other objects, according to the present invention are reached by providing a set comprising a totally implantable device for electroneuromodulation for the electric stimulation of the nervous tissue of the wall of the stomach and/or another neuroreceptive biological tissue, and an implantation tool of said device, characterised in that said tool comprises an axially hollow longitudinal containment body for said device and a needle incorporated into said containment body and having a tip that projects forwards to a sharp front end of said containment body, said needle being connected to a supply conduit of a fluid injectable from said needle into the tissue for the creation of a localised tissue swelling in which said device can be positioned.

Advantageously the device also has independent production means of the electrical energy necessary for the generation of electric pulses for stimulation and/or for other functions.

The independent production means of electrical energy preferably comprise at least one piezoelectric longitudinal element external to the device for the recovery of electrical energy from the natural movement of the tissue inside which the device is implanted.

Preferably the piezoelectric longitudinal element is constrained only at one of its ends to the device.

Preferably the needle extends along the axial generatrix of the containment body that passes through the most advanced point of the front end of said containment body.

Preferably the needle extends at a thickening of the containment body.

Preferably the containment body has a base at the rear from which a rigid tubular connection extends at the rear communicating with the inside of the containment body through a through opening of the rear base of the containment body.

Preferably the supply conduit is formed by a hose.

Preferably the supply conduit extends into said rigid tubular connection through the opening of the rear base of the containment body.

Preferably a piston is provided for ejecting the device slidable in the containment body and having a flexible activation cable which extends into said rigid tubular connection through the opening of the rear base of the containment body.

Preferably the device for electroneuromodulation has a cylindrical shape with rounded front and rear ends.

Preferably in the configuration wherein the piston is at its end stroke within the containment body and the device is resting against the piston, the rounded front end of the device is at least partially outside said sharp front end of the containment body.

Preferably the device for electroneuromodulation has on its external surface one or more electrodes without electrocatheters external to the device itself.

The invention also discloses a positioning method of a device for the electroneuromodulation of a biological tissue characterised in that it comprises in sequence the steps of:
  providing an implantation tool comprising an axially hollow longitudinal containment body for said device and a needle incorporated into said containment body and having a tip that projects forwards to a sharp front end of said containment body
  positioning said device within said containment body
  transporting into a prefixed tissue area the set comprising the tool with the device positioned within it
  creating an implant site by supplying said needle with a quantity of fluid that is injected into said tissue zone so as to create a localised tissue swelling that acts as the implant site
  making the sharp front end of the containment body penetrate into the implant site thus created;
  ejecting the implant from the containment body so as to position it in the implant site; and
  selectively withdrawing the tool leaving the implant in the implant site.

The fluid used to create the implant site may be water or a physiological solution or a medicated solution.

BRIEF DESCRIPTION OF THE DRAWINGS

Further characteristics and advantages of the invention will more fully emerge from the description of a preferred but not exclusive embodiment of the set comprising a totally implantable device for electroneuromodulation for the electric stimulation of the nervous tissue of the wall of the stomach and/or of another neuroreceptive tissue of the human body, and an implantation tool of said device according to the invention, illustrated by way of non-limiting example in the accompanying drawings, in which:

FIG. 3 shows a raised lateral view of the assembled set;

FIG. 4 shows a raised lateral view of the device for electroneuromodulation and of the piston;

FIGS. 7a, 7b, 7c, 7d, 7e, 7f and 7g show the sequence for using the set of FIG. 8;

DETAILED DESCRIPTION OF THE ILLUSTRATED EMBODIMENTS

Figure 1:
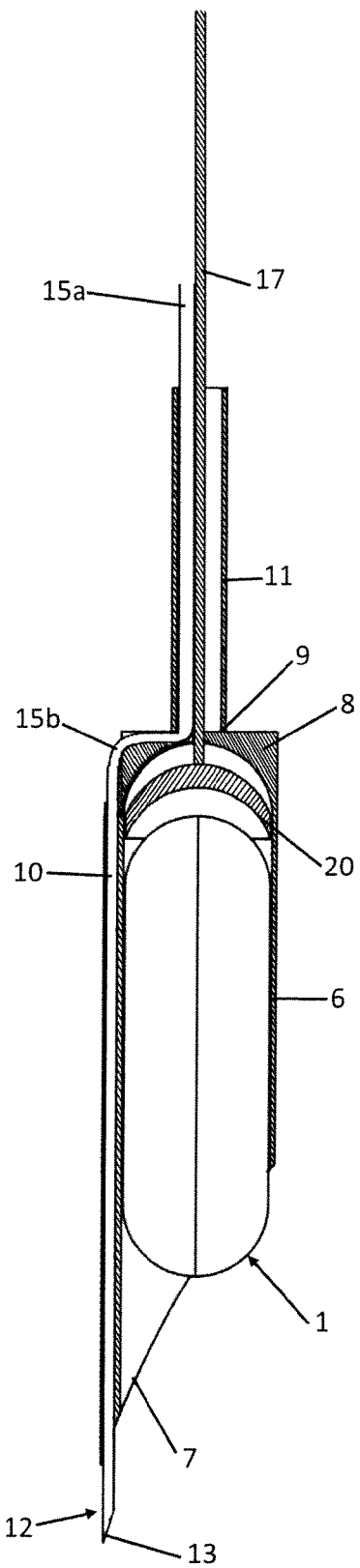
FIG. 1 is a raised lateral view of the set assembled and axially sectioned.
Figure 2:
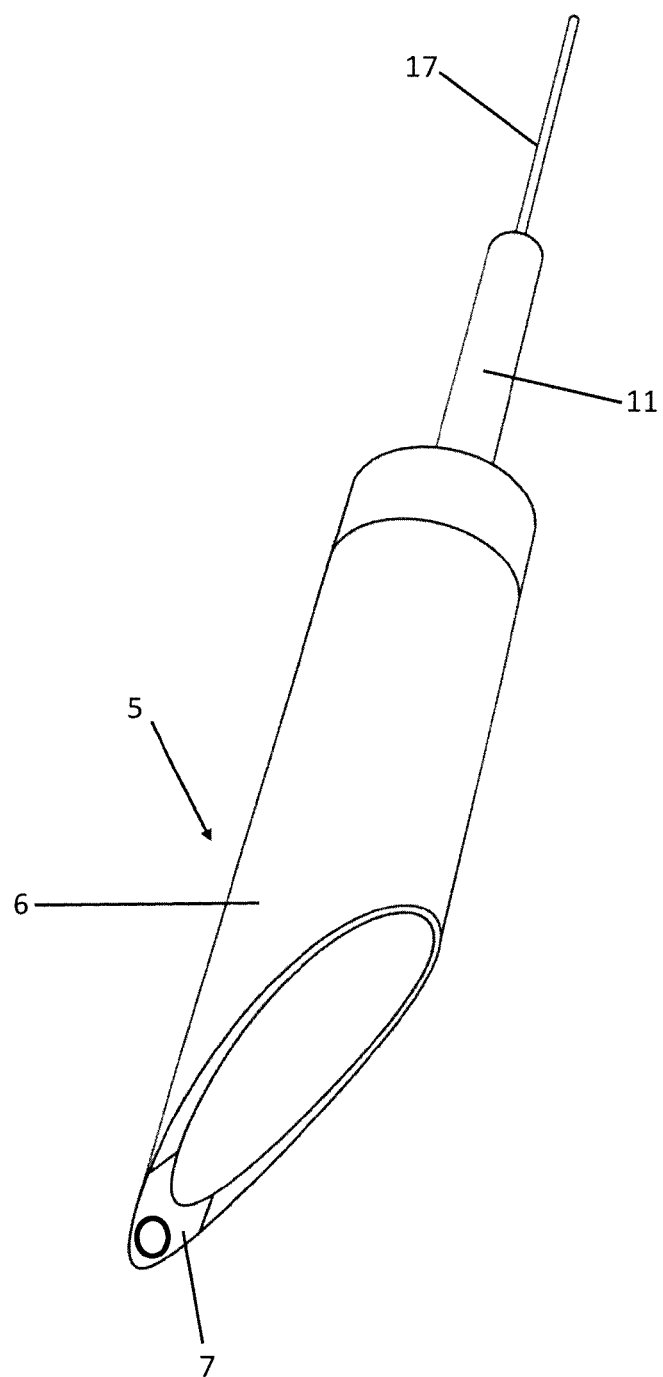
FIG. 2 shows a perspective view of the insertion system of the device in the tissue swelling.
Figure 5:
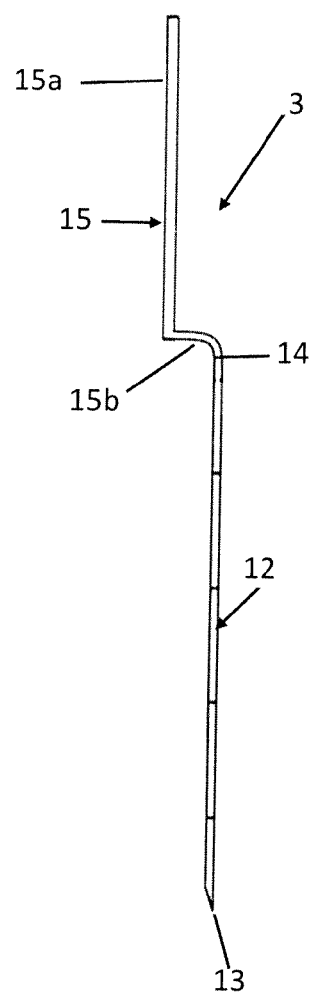
FIG. 5 shows a raised lateral view of the system for creating the tissue swelling comprising the needle connected to the supply conduit.
Figure 6:
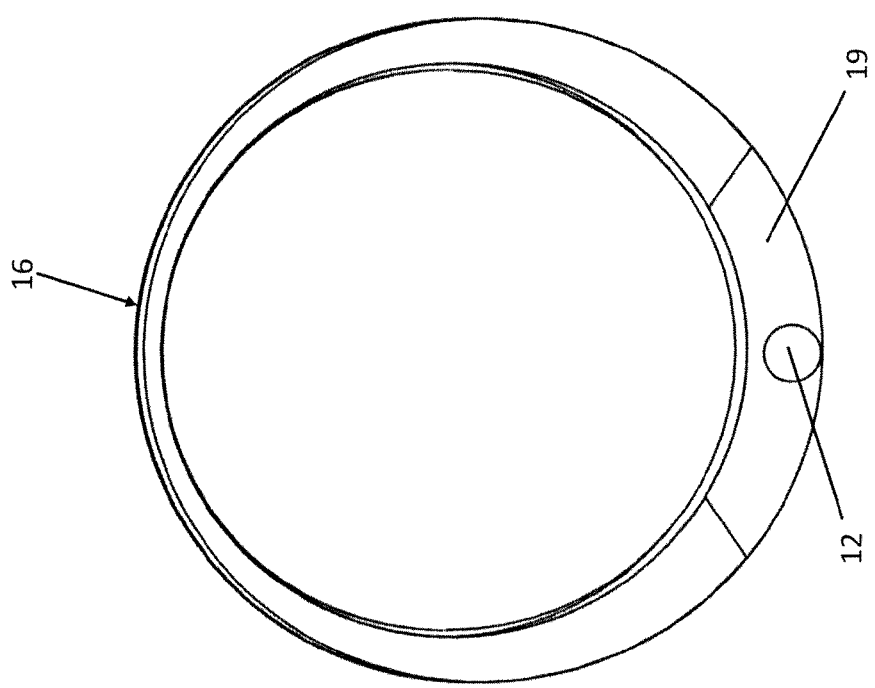
FIG. 6 shows a front view of the set.

The set comprises a totally implantable device 1 for electroneuromodulation for the electric stimulation of the nervous tissue of the wall of the stomach and/or of another neuroreceptive tissue of the human body or an animal's body, and an implantation tool 2 of the device 1.

The tool 2 in turn comprises a system 3 for creating a localised tissue swelling 4 into which the device 1 can be introduced and an insertion system 5 of the device 1 into the swelling 4 that can be made in the gastric mucosa or in other soft tissues.

The set comprising the device 1 and the tool 2 can be transported in situ as we will see by a specific in situ transporting means (not shown) according to the specific application The insertion system 5 comprises an axially hollow longitudinal containment body 6 for the device 1 having an oblique sharp front end 7 and a rear base 8 from which a rigid tubular connection 11 extends at the rear communicating with the inside of the containment body 6 through a through opening 9 of the rear base 8 of the containment body 6. The system 3 for creating the tissue swelling 4, on the other hand, comprises an axially hollow needle 12 incorporated into the containment body 6 and having a tip 13 that projects forwards to the sharp front end 7 of the containment body 6 and a base 14 connected to a supply conduit 15 of a fluid injectable from the needle 12 into the tissue for creating the tissue swelling 4.

The needle 12 extends along the axial generatrix of the containment body 6 that passes through the most advanced point of the front end 7 of the containment body 6 itself.

In particular, the needle 12 extends at a thickening 19 of the containment body 6.

The containment body 6 has an internal and external cylindrical conformation.

The circular profile of the internal cross section is not concentric with the circular profile of the external cross section of the containment body 6 so as to create the thickening 16 without changing the internal and external cylindrical conformation of the containment body 6 necessary for the containment body 6 in order to penetrate into the tissue correctly without causing unnecessary lacerations.

The system 5 for inserting the device into the swelling 4 also comprises a piston 16 for ejecting the device 1 mobile within the containment body 6.

Between the lateral wall of the piston 16 and the internal wall of the containment body 6 fluid sealing means are provided, for example a toroidal gasket, to prevent the return of organic fluid, in particular blood, towards the connection 11 during the penetration of the tool 2 into the tissue.

The piston 16 has a flexible activation cable 17 which extends into the rigid tubular connection 11 through the opening 9 of the rear base 8 of the containment body 6.

The end stroke of the piston 16 inside the containment body 6 is defined by an internal abutment 10 of the containment body 6 adjacent to the rear base 8 and having a conjugated shape to the piston 16.

In the configuration of the set in which the piston 16 is at its end stroke inside the containment body 6 and the device 1 is resting against the piston 16, the rounded front end of the device 1 is at least partially outside the sharp front end 7 of the containment body 6. Thanks to this configuration of the set during the penetration of the tool 2 into the tissue, also the rounded front end of the device 1 defines a sliding surface that cooperates for the divarication without lacerations of the tissue. With specific reference to the embodiment illustrated in FIG. 8 the piston 16 has a hole 21 for the passage of at least one piezoelectric longitudinal element 22, for example a wire or a lamina, with which the device 1 is externally provided. The piezoelectric longitudinal element 22 is only constrained at one of its ends to the device 1, in particular but not necessarily at the rear end of the device 1. The piezoelectric element 22 enables the necessary energy to be recovered for the operation of the device 1.

The supply conduit 15 is formed by a hose and comprises a first portion 15a that extends into the connection 11 and a second connecting portion 15b between the first portion 15a and the base 13 of the needle 12.

The following description refers to the implant of the device 1 in the intragastric wall, the so-called mucosa. A similar approach may be used for implantation in other sites of the body (human or animal) with the sole replacement of the in situ transporting means, or for the implantation of other devices as long as they have the characteristics of having a suitable shape to operate with the tool 2.

The needle 12, thanks to its conformation and arrangement, can be brought into contact with the wall in which the implantation takes place, in the case in question the gastric mucosa, is able to penetrate the mucosa by a few millimeters, and allows the injection of the fluid adapted, prevalently but not exclusively, to create the tissue swelling 4, or sufficient space for the subsequent insertion of the device 1.

The insertion system 5 allows penetration into the tissues thanks to the sharp front end 7 of the containment body 6 and with the help of the divarication provided by the front end of the device 1.

After the creation of the swelling 4 and sufficient penetration of the insertion system 5 into the tissues, the tool 2 housing the device 1 is pushed into the tissues by means of the piston 16, while the in situ transporting means is withdrawn from the tissues. After the extraction of the transporting means from the tissues, the insertion system 5 is also withdrawn. These operations are performed in this sequence to prevent the risk of the device 1 coming out of the tissues.

To enable the above, the containment body 6 must also be able, as well as to contain the device 1, to allow the penetration into the tissue through the front end 7, to eject the device 1 by means of the piston 16 controlled by the thrust cable 17 once the implant location has been reached and to support the tissue swelling creation system 3, while the rear end 8 of the containment body 6 must be able to strike against the in situ transporting means and provide a suitable support to allow the thrust and direction of the tool 2 housing the device 1 within the tissue, guarantee the passage of the thrust cable 17 that controls the ejecting piston 16 and guarantee the passage of the supply conduit 15.

The device 1, present inside the containment body 6 of the tool 2 for the whole of the first step of the implantation procedure, before the functions that it will perform once the procedure has been completed, is specifically conformed to operate with the implantation tool 2, with the front end facing the implant site having a rounded morphology as mentioned conformed so as to make the shape of the whole set harmonic, and to allow the gradual divarication of the tissues that would otherwise be torn, cut or suffer further unnecessary lesions.

The device 1 is equipped with specific roughness and an external composition, with different characteristics from the implant site, specifically to prevent any displacement or bedsores.

The device 1 may have at its rear end, also with a rounded shape, a lace that lies outside the tissues englobing the device 1 itself once the positioning is complete, in order to facilitate any extraction operations.

The device 1 is preferably comprised of at least three main connected sections, built and coupled in order to produce the electric stimulation of the actual body tissues adjacent to the stimulator.

A first section comprises the electrodes, with a number and position functional to the type of stimulation and communicating with the outside of the device.

A second section comprises the circuits that house the memories, hardware and software required by the device for processing the necessary information for the stimulation, storing data on the operation of the device itself, related to the tissue and/or the body stimulated and related to the serial number of tie device, as well as the antenna required for active and passive communication with the outside.

A third solution comprises the device's energy self-supply system.

This system, regardless of its type, has the function of making the device energy independent, making it independent from the use of non-rechargeable batteries or external devices adapted for direct power supply or recharging. This system may vary in its shape, size and position, and may also be partly external to the device itself.

The electrical energy recovered may be exploited for passive functions, for example for recording and storing data, and/or active functions, for example for electric stimulation.

Figure 8:
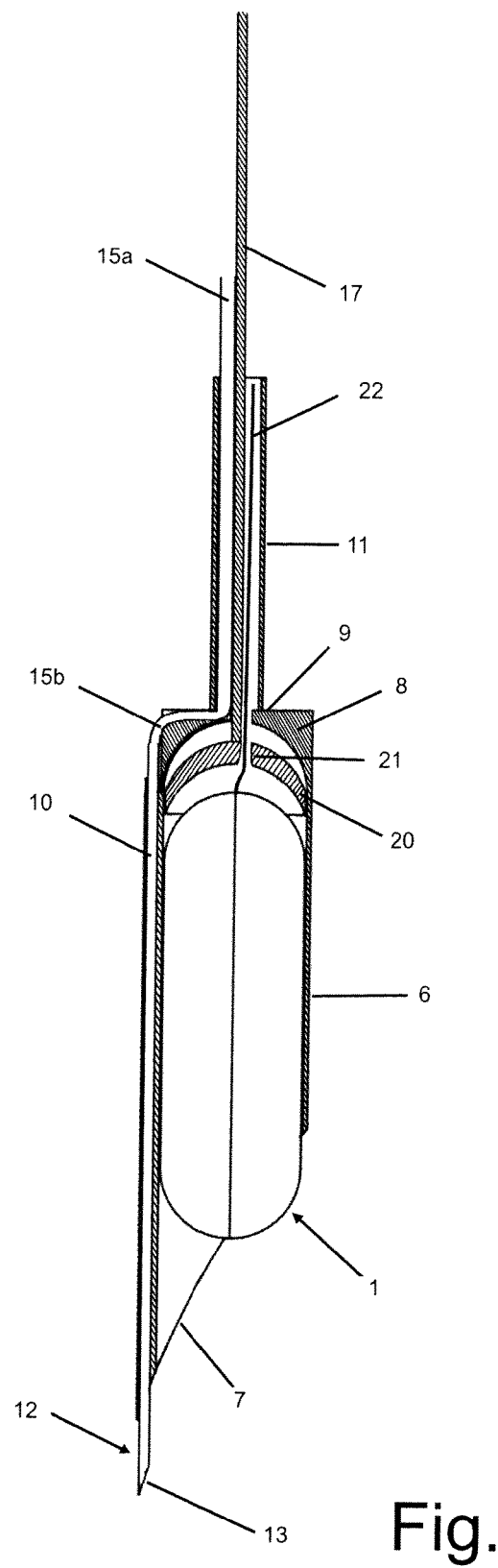
FIG. 8 is a raised lateral view of another preferred embodiment of the set assembled and axially sectioned.

This system can be of various kinds, but is preferably of the piezoelectric type such as the one described in the embodiment of FIG. 8.

According to the application the piezoelectric energy recovery element, positioned outside the device 1, exploits the mechanical energy deriving from the natural movement of the tissues in which it is positioned, e.g. the mechanical energy deriving from the peristalsis of the digestive system.

The energy self-supply system may also be in other applications of the biomechanical, biochemical or thermal type or a combination of different types.

Among the possible additional sections of the device 1 a communication and data exchange section with the outside may be provided that does not use energy sources internal to the device 1, e.g. by exploiting RFID technology.

The in situ transporting means of the tool 2 with the device 1 inside may be different according to the different implant sites.

The in situ transporting means may be an endoscope in the event of insertion into the gastric mucosa. In this case the supply conduit of the fluid 15 and the cable 17 pass through the operating channel of the endoscope into which in its final part the rigid connection 11 is inserted provided by the containment body 6.

The in situ transporting means may also be defined by a handle that allows the tool 2 to be used with the device 1 inserted for inserting the device 1 in other zones of the body.

The procedure for using the complete system appears clear from the above description and is briefly as follows.

The tool 2 with the device 1 inserted is taken in proximity to the tissue where the insertion will take place.

The system 3 is inserted for creating the swelling 3 in the soft tissue, e.g. in the gastric mucosa.

Through the system 3 for creating the swelling 4 the fluid is injected with which the swelling 4 is created.

The insertion system 5 is pushed into the soft tissue.

Through the piston 16 the insertion system 5 deposits the device 1 into the soft tissue.

The insertion system 5 is withdrawn.

The device 1 is deposited into the appropriate site for stimulation.

Once the implantation is complete the device 1 lies completely within the tissues, while the lace crosses the wall lying outside them.

The piezoelectric element 22, in the event that for example the device 1 is implanted in a tissue of a hollow digestive organ with propulsive activity, is activated by the natural movement of the organ itself to recover electrical energy.

The device 1 more precisely modulates the autonomic nervous system, particularly the sympathetic/parasympathetic balance through electric stimulation of the neuromuscular tissue of the stomach and the digestive system, obtained by administering electric pulses generated by the pulse generator. The pulse generator is designed to guarantee the production of parameters of outgoing electric stimulation, based on the characteristics of the neurovegetative response of the subject being treated. The personalised electric stimulation parameters allow the most effective stimulation to be used to modulate the neurovegetative system, i.e. the sympathetic/parasympathetic ratio.

The body of the device 1 has a functional shape to the implant; in the case in question it has a cylindrical shape which is functional to the introduction into the stomach through the oral cavity with a gastroscope (avoiding all types of scars on the abdominal cutis) to be localised definitively in the thickness of the gastric wall. Once inserted in the gastric wall, the device 1 remains in place thanks to its surface shape and finish, and thanks to the spontaneous closure of the gastric mucosa in the step straight after implantation. The lace remains visible outside the stomach to be used in the event of removing the device 1 to apply traction thereto; the ejection of the device 1 is also operated endoscopically, through a gastroscope equipped according to the purpose, with equipment that is morphologically suitable for being coupled to the lace lying in the stomach. The lace lying within the gastric lumen does not imply any disturbances or changes to the functionalities of the digestive system itself.

As has been mentioned, thanks to the presence of the generator inside the device 1, with the peristaltic movements of the stomach, with the vibrations of visceral arterial vascular pulsatility and the actual movements (walking or running) of the body or other potential sources of energy such as the body temperature or the chemical or biological composition of the tissues, the production of the necessary electrical energy for the stimulation and operation of the device 1 is guaranteed. Stimulation is not guaranteed only by the electrical pulse of the mechanical component of the intraparietal dimension of the item itself.

The device 1 is positioned directly in the stimulation site and is therefore free from an electrocatheter, hence avoiding all problems resulting from their presence.

The device 1 also guarantees a long life and durability since the battery does not need to be replaced, having the independent production of electrical energy.

The set comprising a totally implantable device for electroneuromodulation for electric stimulation of the nervous tissue of the wall of the stomach and/or of another neuroreceptive tissue of the human body thus conceived is susceptible of numerous modifications and variants, all falling within the scope of the inventive concept; furthermore, all the details are replaceable by technically equivalent elements. The materials used, as well as the dimensions, may in practice be of any type according to requirements and the state of the art.

The invention claimed is:

1. A set comprising:
   a totally implantable device for electroneuromodulation for the electric stimulation of a neuroreceptive biological tissue; and
   an implantation tool of the device, comprising:
      an axially hollow longitudinal containment body for the device; and
      a needle incorporated into the containment body and having a tip that projects forward to a sharp front end of the containment body, the needle being connected to a supply conduit of a fluid injectable from the needle into the neuroreceptive biological tissue for the creation of a localized tissue swelling in which the device can be positioned;
      where the containment body has a base at a rear thereof from which a rigid tubular connection develops and communicates with an inside of the containment body through a through opening of the base of the containment body, the supply conduit extending into the rigid tubular connection through the through opening of the base of the containment body.

2. The set of claim 1, wherein the device further comprises independent electrical energy production means necessary for the generation of electric pulses for stimulation or for other functions.

3. The set of claim 2, wherein the independent electrical energy production means comprises at least one piezoelectric longitudinal element external to the device for recovery of electrical energy from natural movement of the tissue inside which the device is implanted.

4. The set of claim 1, wherein the needle develops along an axial generatrix of the containment body which passes through a most advanced point of the sharp front end of the containment body.

5. The set of claim 1, wherein the containment body has an internal circular cross section and an external circular cross section, the internal circular cross section being non-concentric with the external circular cross section to define a thickening of the containment body, where the needle develops at the thickening of the containment body.

6. The set of claim 1, further comprising:
   a piston for ejecting the device slidably in the containment body; and
   a flexible activation cable which extends into the rigid tubular connection through the through opening of the rear of the base of the containment body.

7. The set of claim 6, having a configuration wherein, when the piston is fully retracted within the containment body, with the device resting against the piston, a front end of the device is at least partially outside the sharp front end of the containment body.

* * * * *